United States Patent [19]

Fong et al.

[11] Patent Number: 4,604,213

[45] Date of Patent: Aug. 5, 1986

[54] POLYMERS OF 1-ACRYLOYL-4-METHYL PIPERAZINE, METHYL CHLORIDE OR SULFATE QUATERNARY SALTS AS FLOCCULANTS

[75] Inventors: Dodd W. Fong, Naperville; Ann M. Halverson, Wheaton, both of Ill.

[73] Assignee: Nalco Chemical Company, Oak Brook, Ill.

[21] Appl. No.: 720,848

[22] Filed: Apr. 8, 1985

[51] Int. Cl.$^4$ ........................ C02C 1/56; B01D 21/01
[52] U.S. Cl. .................................. 210/735; 210/736; 544/399
[58] Field of Search ................. 210/735, 736; 544/399

[56] References Cited

U.S. PATENT DOCUMENTS

| | | | |
|---|---|---|---|
| 2,843,573 | 7/1958 | Melamad | 526/291 |
| 3,284,393 | 11/1966 | Vanderhoff et al. | 260/29.6 |
| 4,305,829 | 12/1981 | Kelsey | 210/735 |

OTHER PUBLICATIONS

Ca 85:51751h, German Offer. 2,546,240, Ferruti et al.

Primary Examiner—John Kight
Assistant Examiner—M. L. Moore
Attorney, Agent, or Firm—John G. Premo; Donald G. Epple

[57] ABSTRACT

Polymers of certain quaternary ammonium salts of 1-acryloyl-4-methyl piperazine are excellent flocculants for suspended solids present in aqueous industrial wastes.

6 Claims, No Drawings

POLYMERS OF 1-ACRYLOYL-4-METHYL PIPERAZINE, METHYL CHLORIDE OR SULFATE QUATERNARY SALTS AS FLOCCULANTS

INTRODUCTION

It is now known that water-soluble polymers are useful as flocculants for a variety of aqueous industrial waters which contain suspended solids. In certain areas such as mining, sewage, and the like, particularly effective flocculants are water-soluble homo and copolymers which are cationic. An effective coagulant for removing suspended solids from a variety of industrial wastes are the homopolymers of diallyl dimethyl ammonium chloride (DADMAC).

If it were possible to provide an improved cationic flocculating agent that gave results that were superior to DADMAC, an improvement in the art would be afforded.

THE INVENTION

The invention resides in a method of flocculating suspended solids from aqueous industrial wastes which comprises treating said wastes with a small, yet effective, amount of a water-soluble polymer which contains at least 50 mole percent of either the dimethyl sulfate or the methyl chloride quaternary ammonium salt of 1-acryloyl-4-methyl piperazine (AMPIQ), which polymer has an intrinsic viscosity greater than 0.5.

Homopolymers of the type described above, e.g. the dimethyl sulfate or methyl chloride quaternary ammonium salts of AMPIP are preferred. The copolymers with up to 50 mole percent of acrylamide represent a preferred species of copolymers.

Monomers other than acrylamide may be copolymerized with AMPIQ. These co-monomers may be either nonionic, cationic, or anionic. Examples of suitable nonionic monomers include: methacrylamide, acrylonitrile, vinyl acetate, lower alkyl acrylates, lower alkyl methacrylates, N-alkyl acrylamides, styrene, etc. Examples of suitable anionic co-monomers useful in this invention include: acrylic acid, methacrylic acid, itaconic acid, maleic anhydride, acrylamidomethylpropanesulfonic acid, etc. Examples of suitable cationic monomers which may be useful in this invention include: dimethylaminoethylacrylate, quaternary salts of dimethylaminoethylacrylate, dimethylaminoethylmethacrylate, dimethylaminoethylmethacrylate quaternaries, diallyldimethylammonium chloride, methacrylamidopropyltrimethylammonium chloride, N-vinyl pyrrolidone, vinyl pyridine, N,N-dimethylaminomethylacrylamide, N,N-dimethylaminomethylmethacrylamide, N,N-dimethylaminomethylacrylamide quaternaries, etc. It is understood the resultant copolymer should be water-soluble.

Preferred in the practice of the invention is the utilization of the polymers or copolymers which have an intrinsic viscosity greater than 0.5 and, preferably, those having an intrinsic viscosity of at least 1 or more.

To illustrate the preparation of the AMPIQ monomers, the following are presented by way of example:

EXAMPLE 1

1-Acryloyl-4-Methyl Piperazine.

A mixture of acryloyl choride (102.0 g, 1.13 moles) in methylene chloride (100 ml) was added dropwise into a solution of N-methyl piperazine (86.0 g, 0.86 moles) in methylene chloride (450 ml) over a period of one hour. During the addition, the temperature of the N-methyl piperazine/methylene chloride was kept below 25° C. After the addition was complete, the reaction mixture was stirred at room temperature for two hours. The reraction mixture was neutralized with 260 g of 17% sodium carbonate solution. The organic layer containing the crude product was separated from the aqueous layer via a separatory funnel. The aqueous layer was washed well with methylene chloride. Combination of the organic phases and rotoevaporation of the solvent yielded 100.0 grams of crude product. Distillation of the crude product yield a fraction (74°–78° C./5 mm Hg) that was >98% by G.C. analysis. $^{13}$C nmr and IR analysis gave spectra consistent with the title compound.

EXAMPLE 2

Dimethyl sulfate (23.2 g) was added slowly into an AMPIP (30.0 g), water (51.8 g) mixture. The temperature of the reaction mixture was kept below 30° C. After complete addition, the reaction mixture was stirred for 2 hours. A $^{13}$C nmr spectram was consistent with the title compound.

Into a 300 ml Parr bomb was charged 26.6 g. water, 21 g. 1-acryloyl-4-methyl piperazine, and 10 g. methyl chloride. The valves were closed and the bomb was heated to and maintained at 60° C. until no more methyl chloride was taken up. The product was characterized by $^{13}$C nmr.

As will be shown hereinafter, the polymers are conveniently prepared using either solution polymerization or the so-called "inverse emulsion polymerization" method which utilizes polymerization of water-soluble vinyl monomers in the form of water-in-oil emulsions. This technique is described in Vanderhoff, U.S. Pat. No. 3,284,393, the disclosure of which is incorporated herein by reference.

A typical polymerization using the so-called "inverse emulsion" technique is set forth below as Example 3.

EXAMPLE 3

Water-in-Oil Emulsion Polymerization of Acrylamide and AMPIPQUAT

| Oil Phase: | |
|---|---|
| LOPS[1] | 130.0 g |
| Sorbitan Monooleate | 7.5 g |
| 4 moles EO reacted with Sorbitan Monostearate | 2.5 g |
| Aqueous Phase: | |
| 50% AMPIP MSQ[2] | 51.25 g |
| 46.4% Acrylamide solution | 246.49 g |
| H$_2$O | 49.92 g |
| Ethylene diamine tetraacetic acid | .05 g |
| Initiator: | |
| 2,2'-Azobisisobutyronitrile | .28 g |

[1]LOPS = A low odor paraffin solvent.
[2]AMPIP MSQ = 1-acryloyl-4-methyl piperazine dimethyl sulfate quaternary ammonium salt.

The oil and the aqueous phases (pH 5) were first prepared and the emulsion was obtained by adding the aqueous solution into the LOPS solution with vigorous stirring.

The emulsion was purged with nitrogen for ½ hour and then heated to 45° C. The initiator was added. The reaction was maintained at 45° C. for four hours and at 65° C. for one hour. The reaction was cooled to room temperature. G.C. analysis of the residual monomer shows the polymerization was 74% complete. IV of the copolymer was 7.0.

Typical solution polymerizations are prepared below as Examples 4, 5, and 6.

EXAMPLE 4

50% AMPIQ in water (20.0 g), $H_2O$ (70.8 g), and 2% ethylene diamine tetra-acetic acid (2 ml) were combined in a 200 ml resin kettle and heated to 60° C. under a blanket of nitrogen gas. The monomer solution was initiated with ammonium persulfate (0.7 g in 5 ml $H_2O$) and the reaction mixture maintained at 60°–65° C. for 3 hours. The temperature was then raised to 70° C. for 1 hour. The resulting polymer had an intrinsic viscosity of 0.23. Residual monomer (920 ppm) was noted.

EXAMPLE 5

50% AMPIQ (20 ml), 2% ethylene diamine tetra-acetic acid (1 ml), 25% sodium formate (0.25 g) and $H_2O$ (74.75 ml) were combined in a 200 ml resin kettle. The reaction was run as per Example 4 except 2,2′-Azo bis 2-amidino propane hydrochloride (0.03 g in 4 ml $H_2O$) was used as the initiator. The reaction was heated for 5 hours at 45° C. The resulting polymer had an intrinsic viscosity of 1.78.

EXAMPLE 6

To produce a polymer having an intrinsic viscosity of 1.37, Example 5 was repeated except 1.6 g of a 25% sodium formate solution was used.

The amount of the homo or copolymers necessary to produce good flocculation will vary depending upon the type of solids treated, their amount, and the nature of the water in which they are suspended. In many cases, dosages as little as ½–3 ppm of polymer will give good flocculation although dosages as high as 50 ppm may be required in some instances. The best results are achieved when the suspended solids are predominantly inorganic in nature.

Using the above techniques, different intrinsic viscosities AMPIP dimethyl sulfate quaternary ammonium salt homopolymers were tested to compare their activity against commercial homopolymers of diallyl dimethyl ammonium chloride. The commercial polymers contained approximately 20% active polymer.

The test consisted of using a so-called "standard Kaolin jar test" to evaluate the efficacy of the polymers as flocculants. This test was run in accordance with the following procedure:

NATURAL WATER

1. Fill beakers with 250 or 500 ml of water (amount varies according to gang-stirrer used).
2. Place beakers on gang-stirrer and set speed at 20 rpm.
3. Dose beakers with appropriate quantity of coagulant.
4. Set speed at 100 rpm for five minutes.
5. Reset speed at 50 rpm for ten minutes.
6. Remove beakers and allow to stand for fifteen minutes.
7. Withdraw a twenty-five ml aliquot and read turbidity. (Note: Aliquot should be withdrawn one cam below center of sample surface.)

SYNTHETIC WATER

The procedure for jar testing using synthetic water is as above with the following exceptions:
1. Only distilled water to which 2 ml of Kaolin has been added is used.
2. Sample must stand for twenty-five minutes.

The results were reported in terms of Replacement Ratio which indicates the amount of test polymer required to give results similar to polyDADMAC. The polymers were tested on an actives basis.

The results of these tests are presented below in Table I. From Table I it is evident that the polymers of the invention having an intrinsic viscosity greater than 1 are better than the polyDADMAC.

TABLE I

| Sample Number | Wt. % Solids | Intrinsic Viscosity, cp. | Replacement Ratio |
|---|---|---|---|
| Example 4 | 9.54 | 0.23 | 1.45 |
| Example 5 | 9.35 | 1.78 | 0.90 |
| Example 6 | 9.7 | 1.37 | 0.93 |
| PolyDADMAC | 20.0 | .5 | 1 |

Having thus described our invention, it is claimed as follows:

1. A method of flocculating suspended solids from aqueous industrial wastes which comprises treating said wastes with a small, yet effective, amount of a water-soluble polymer which contains at least 50 mole percent of either the dimethyl sulfate or the methyl chloride quaternary ammonium salt of 1-acryloyl-4-methyl piperazine, which polymer has an intrinsic viscosity greater than 0.5.

2. The method of claim 1 where the suspended solids are predominently inorganic solids.

3. The method of claim 1 where the polymer is a homopolymer.

4. The method of claim 1 where the polymer is a copolymer.

5. The method of claim 3 where the homopolymer is the dimethyl sulfate quaternary ammonium salt of 1-acryloyl-4-methyl piperazine.

6. The method of claim 4 where the copolymer is an acrylamide copolymer.

* * * * *